United States Patent
Hsu et al.

(10) Patent No.: US 6,340,465 B1
(45) Date of Patent: Jan. 22, 2002

(54) LUBRICIOUS COATINGS FOR MEDICAL DEVICES

(75) Inventors: Li-Chien Hsu, Mission Viejo; Can B. Hu, Irvine, both of CA (US)

(73) Assignee: Edwards Lifesciences Corp., Irvine, CA (US)

( * ) Notice: Subject to any disclaimer, the term of this patent is extended or adjusted under 35 U.S.C. 154(b) by 0 days.

(21) Appl. No.: 09/290,501

(22) Filed: Apr. 12, 1999

(51) Int. Cl.$^7$ .......................... A61K 9/00; A61K 47/32; A61K 31/06
(52) U.S. Cl. .................. 424/400; 424/422; 514/772.3; 514/772.4
(58) Field of Search ................ 424/422, 448, 424/400; 523/122; 527/2; 514/772.3, 772.4

(56) References Cited

U.S. PATENT DOCUMENTS

| | | |
|---|---|---|
| 3,616,935 A | 11/1971 | Love et al. |
| 3,617,344 A | 11/1971 | Leininger et al. |
| 3,634,123 A | 1/1972 | Eriksson et al. |
| 3,717,502 A | 2/1973 | Masuhara et al. |
| 4,118,485 A | 10/1978 | Eriksson et al. |
| 4,229,838 A | 10/1980 | Mano |
| 4,565,740 A | 1/1986 | Golander et al. |
| 4,613,665 A | 9/1986 | Larm |
| 4,720,512 A | 1/1988 | Hu et al. |
| 4,786,556 A | 11/1988 | Hu et al. |
| 4,990,357 A * | 2/1991 | Karakelle et al. ............... 427/2 |
| 5,019,393 A | 5/1991 | Ito et al. |
| 5,049,403 A | 9/1991 | Larm et al. |
| 5,053,048 A | 10/1991 | Pinchuk |
| 5,132,108 A | 7/1992 | Narayanan et al. |
| 5,165,919 A | 11/1992 | Sasaki et al. |
| 5,270,046 A | 12/1993 | Sakamoto et al. |
| 5,308,641 A | 5/1994 | Cahalan et al. |
| 5,348,873 A | 9/1994 | Matsuda et al. |
| 5,417,969 A | 5/1995 | Hsu et al. |
| 5,510,418 A | 4/1996 | Rhee et al. |
| 5,532,311 A | 7/1996 | Sirvio et al. |
| 5,562,922 A | 10/1996 | Lambert |
| 5,563,056 A | 10/1996 | Swan et al. |
| 5,672,638 A | 9/1997 | Verhoeven et al. |
| 5,693,034 A | 12/1997 | Buscemi et al. |
| 5,723,145 A * | 3/1998 | Shikinami et al. ........... 424/448 |
| 5,811,151 A | 9/1998 | Hendriks et al. |
| 5,866,113 A | 2/1999 | Hendriks et al. |
| 5,874,500 A | 2/1999 | Rhee et al. |
| 5,879,697 A | 3/1999 | Ding et al. |
| 5,885,647 A | 3/1999 | Larm et al. |
| 6,054,504 A * | 4/2000 | Dalla Riva Toma ........ 523/122 |

FOREIGN PATENT DOCUMENTS

| | | |
|---|---|---|
| EP | 0480809 A2 | 4/1992 |
| EP | 0832618 A1 | 4/1998 |
| JP | 55136064 | 10/1998 |
| WO | 96/37241 | 11/1996 |
| WO | 97/29160 | 8/1997 |

\* cited by examiner

*Primary Examiner*—Thurman K. Page
*Assistant Examiner*—Blessing Fubara
(74) *Attorney, Agent, or Firm*—John Christopher James; Debra D. Condino; Andrew Chen (57) ABSTRACT

Biocompatible surfaces on medical devices, particularly those formed of synthetic materials, are produced by providing coating compounds having crosslinked regions capable of entrapping biocompatible molecules on the surfaces of medical devices in order to form a stable base layer. The crosslinked base layer is lubricious and is able to function as an entrapping or coupling site for additional biocompatible agents, which agents may be stably incorporated into its crosslinked lattice. Thus, the coatings of the present invention have enhanced lubricity and may also have antimicrobial, protein-repelling, and/or antithrombotic properties. The present invention thus discloses novel, stable, biocompatible coating compositions, devices coated with the compositions of the present invention, methods of making and applying such compounds, and methods of preparing and using devices and apparatus coated with such compositions.

16 Claims, 1 Drawing Sheet

Fig. 1

LUBRICIOUS COATINGS FOR MEDICAL DEVICES

FIELD OF THE INVENTION

The present invention relates to simple-to-manufacture and simple-to-use coatings for use on a wide variety of substrates. In one embodiment, the coatings are especially useful in conjunction with medical devices, particularly devices that may come into contact with a subject's tissues or bodily fluids. The coatings of the present invention are thus useful in implantable or indwelling devices, as well as with devices that come into contact with a subject for a shorter period of time.

BACKGROUND OF THE INVENTION

During recent years, there has been a growing emphasis in the medical field on the use of a variety of materials, including synthetic materials, in devices and apparatus that may come into contact with the body and/or bodily fluids. Examples of synthetics used in medical devices and implants include polyethylene (PE), polytetrafluoroethylene (PTFE), silicone, silicone rubber, polyurethane, Dacron, gelatin-impregnated fluoropassivated Dacron (GIF), stainless steel, polyvinylchloride (PVC), nylon, latex, polystyrene, and fluorinated ethylene-propylene copolymer, to name a few.

Many applications have been developed for the use of synthetic materials in the manufacture of devices for use in all areas of medical treatment. Devices as structurally simple as artificial ocular lenses, as well as devices as complex as dialysis machines, can all be improved or enhanced by use of the within-described coating compositions.

While the use of synthetic materials in medical devices has certain attractive structural, chemical and manufacturing advantages, the use of such materials has created several problems which have plagued medical practitioners, however. For example, while synthetic materials tend to be mechanically stable and chemically inert, they are generally not biocompatible or lubricious, especially when directly exposed to bodily fluids, particularly blood. Moreover, undesirable physiological reactions such as thrombosis or bacterial infection may result because the synthetic surfaces attract proteins and other physiological fluid components which may cause the activation of humoral and cellular components of blood. The problem tends to become more acute as storage time (or implantation time) of the device is increased.

It is well known that the insertion or implantation of medical devices such as catheters and tubing into a patient often results in irritation of the area in immediate contact with the device. The surfaces of these devices are generally not lubricious and are not readily accommodated or tolerated when inserted past or through the mucous membranes or the vascular surfaces of a patient. Thus, surgical or prophylactic application of such a device may cause bleeding, discomfort, and subsequent infection. Moreover, the insertion of devices such as chest tubes or urinary catheters tends to cause an appreciable amount of discomfort to a patient as a result of the frictional resistance encountered during insertion of the device, as well as during any subsequent movement by the patient. Therefore, a coating that enhances the ease of insertion of a medical device, thereby decreasing the risk of injury to a patient, represents an important advancement in the art as well.

Although lubricants may be used to minimize initial friction, they are difficult to keep in place and may complicate handling of the devices. Further, there may be a risk of interaction between the lubricant and the patient. Lubricants that are applied immediately before use still require additional handling by medical personnel. Moreover, some lubricants may react with a previously heparinized surface decreasing the bioactivity of the heparin and reducing its ability to prevent the formation of clots. Similarly, prelubricated surfaces may render it difficult, if not impossible, to incorporate other biocompatible substances into—or coat such substances onto—medical devices and apparatus, as many substances may not adhere to a lubricant-coated surface. Further, the effectiveness of a pre-applied lubricant may diminish over an extended period of time during storage. Thus, a workable solution which does not require the use of additional compounds (e.g. pre-applied lubricants) is most desirable.

Accordingly, it is an object of the present invention to overcome the problems associated with the use of existing devices by providing novel lubricious coatings as well as new methods for producing medical devices, implants, and the like that enhance patient comfort. The present invention is also readily adapted to provide coatings that reduce the risk of infection and/or thrombosis.

The present invention also provides methods for producing coated medical devices, implants, and surfaces whose coatings include bound, yet bioreactive, molecules such as lubricity-enhancing agents, antimicrobial agents, anticoagulants, antibacterials, hormones, and the like. Methods for producing multi-functional surfaces in a simple, economical manner that can be utilized in conjunction with the assembly of single- and multi-component devices are also disclosed herein.

SUMMARY OF THE INVENTION

Coatings which have enhanced lubricious qualities—as well as methods of preparing, applying and using the coatings, and the devices to which the coatings have been applied—are disclosed herein. In addition, coatings which possess antimicrobial properties, antithrombotic properties, or both, are also disclosed, as are methods of preparing, applying and using such coatings.

The coatings of the present invention are sterilizable, stable, biocompatible and non-toxic, particularly during use. In addition, the coatings are durable and are able to maintain their lubricity and stability even after storage, sterilization, or both.

In a preferred aspect, this invention relates to coatings which include coupling agents and polyfunctional polymers which are able to form a crosslinked (or latticed) coating and are capable of entrapping hydrophilic and/or lubricious compounds. This capacity confers or enhances the lubricious quality of the coatings. In another aspect, this invention relates to lubricious coatings that include one or more biocompatible compounds that are capable of being coated upon or entrapped within the lattice of the coating.

In general, the present invention accomplishes these and other objectives by providing novel methods for producing devices which have stable, lubricious biocompatible surfaces. These surfaces may additionally contain other biologically active substances that make the surface even more multi-functional—for example, the coatings or surfaces of the present invention may include antimicrobial and/or anti-thrombogenic compositions.

Such surfaces are produced by coating medical devices—regardless of the composition of the device—with unique transitional coatings formed of compositions that are wettable. As a result, the biocompatible surfaces of the present invention are lubricious and may also be designed to be antimicrobial, protein-repelling and antithrombogenic at the earliest phases of the protein cascade effect.

Thus, in one embodiment, the invention discloses a stable, lubricious, biocompatible coating composition comprising a coupling agent, a polyfunctional polymer and at least one biocompatible agent, wherein the coupling agent and the polymer interact to form a three-dimensional crosslinking network which is capable of entrapping the biocompatible agent. The coatings of the present invention are particularly useful when applied to the surface of an apparatus or device, wherein the coupling agent component of the coating is capable of chemically linking the polyfunctional polymer to the surface of a device. In various preferred embodiments, the device or apparatus is a medical device.

The invention also discloses coating compositions wherein the polyfunctional polymer has two or more functionalities, as well as compositions in which the polyfunctional polymer has an equivalent weight of 100 or less. In variations of the invention, the polyfunctional polymer is selected from the group consisting of polyethylenimine, polyvinyl alcohol, polyacrylic acid, and polyacrylamide.

In another variation of the invention, the coupling agent has an epoxy functionality of two (2) or greater. In one embodiment, the coupling agent comprises one or more epoxides. The one or more epoxides may be polyepoxides or polyglycidyl ether compounds. In embodiments where the epoxides are polyglycidyl ether compounds, they may be selected from the group consisting of diglycidyl ethers, triglycidyl ethers, and tetraglycidyl ethers.

In various embodiments of the present invention, the one or more epoxides are selected from the group consisting of sorbitol polyglycidyl ether, polyglycerol polyglycidyl ether, pentaerythritol polyglycidyl ether, diglycerol polyglycidyl ether, triglycidyl tris(2-hydroxyethyl)isocyanurate, glycerol polyglycidyl ether, trimethylolpropane polyglycidyl ether, resorcinol diglycidyl ether, glycidyl ester ether of p-hydroxybenzoic acid, hydroquinone diglycidyl ether, neopentyl glycol diglycidyl ether, 1,6-hexancdiol diglycidyl ether, bisphenol A (PO)$_2$ diglycidyl ether, bisphenol S diglycidyl ether, hydrogenated bisphenol A diglycidyl ether, ethylene polyethylene glycol diglycidyl ether, propylene polypropylene glycol diglycidyl ether, polytetramethylene glycol diglycidyl ether, adipic acid diglycidyl ester, terephthalic acid diglycidyl ester, o-phthalic acid diglycidyl ester, and higher dicarboxylic acid diglycidyl ester.

The present invention further discloses coating compositions in which the coupling agent is selected from the group consisting of isocyanates, aldehydes and carbodiimides. In various alternative embodiments, the isocyanates are selected from the group consisting of toluene diisocyanate, diphenylmethane diisocyanate, dicyclohexylmethane diisocyanate, and hexamethylene diisocyanate.

Another variation of the present invention discloses coating compositions wherein the biocompatible agent is a hydrophilic polymer. In various embodiments, the hydrophilic polymer is selected from the group consisting of polyvinylpyrrolidone (PVP), PVP/vinyl acetate copolymer, and polyethylene oxide.

In another embodiment of the invention, the biocompatible agent is an antithrombogenic or anticoagulant agent, such as heparin, heparin complex, or a heparin-like compound. In still another embodiment, the biocompatible agent is selected from the group consisting of: antibacterial (or antimicrobial) agents, antihistamines, anti-inflammatory agents, anticholinergic agents, antiparasitic agents, antiviral agents, inhibitors, diagnostic agents, ophthalmic agents, chelating agents, immunosuppressive agents, antimetabolites, anesthetics, antifungal agents, amoebicidal agents, trichomonacidal agents, analgesic agents, antiarthritic agents, antiasthmatic agents, anticonvulsants, antidepressants, antidiabetic agents, antineoplastics, antipsychotic agents, antihypertensive agents, muscle relaxants, proteins, peptides, hormones and lubricating agents.

The present invention also discloses a variety of methods, including a method of preparing a stable, lubricious, biocompatible coating on the surface of a medical device, comprising:
  (a) contacting the surface with a coupling agent under predetermined conditions;
  (b) contacting the surface with an admixture comprising a polyfunctional polymer and at least one biocompatible agent under predetermined conditions; and
  (c) allowing the coupling agent and the admixture to interact for a time period sufficient to form a coating having a crosslinked configuration.

The invention further provides a number of predetermined conditions which are relevant to the methods disclosed herein. Thus, in one exemplary embodiment, the predetermined conditions comprise a temperature in the range of 15–95° C.; in another embodiment, the predetermined conditions comprise a temperature in the range of 20–65° C.

In another embodiment, the invention discloses a method of preparing a stable, lubricious, biocompatible coating on the surface of a medical device, comprising:
  (a) contacting the surface with an admixture comprising a polyfunctional polymer and at least one biocompatible agent under predetermined conditions;
  (b) contacting the surface with a coupling agent under predetermined conditions; and
  (c) allowing the coupling agent and the admixture to interact and to form a coating having a crosslinked configuration.

In yet another variation, the invention discloses a method of preparing a stable, lubricious, biocompatible coating on the surface of a medical device, comprising:
  (a) contacting the surface with a coupling agent, a polyfunctional polymer and at least one biocompatible agent under predetermined conditions; and
  (b) allowing the coupling agent, the polymer and the biocompatible agent to interact to form a coating having a crosslinked configuration.

In various embodiments, the biocompatible agent is an antithrombogenic or anticoagulant agent. For example, the biocompatible agent may be heparin, heparin complex, a heparin-like compound, or any combination of the foregoing.

The present invention also discloses apparatus and devices—e.g. medical devices—having a stable, lubricious, biocompatible coating formed thereon, the coating comprising a coupling agent, a polyfunctional polymer and at least one biocompatible agent, wherein the coupling agent and the polymer interact to form a three-dimensional crosslinking network capable of entrapping the biocompatible agent. In one embodiment, the polyfunctional polymer is chemically linked to the surface of the medical device by the coupling agent. In various additional embodiments, the polyfunctional polymer preferably has an equivalent weight of 100 or less. In various alternative embodiments, the polyfunctional polymer is selected from the group consisting of polyethylenimine, polyvinyl alcohol, polyacrylic acid, polyacrylamide, and combinations thereof.

In another variation of the present invention, the device comprises one or more synthetic materials. Exemplary synthetic materials include plastics, composites, resins, metals, ceramics, carbonaceous materials, silicones, rubbers, polyethers, polysulfones, polyamides, polyimides, polyurethanes, polycarbonates, polyesters, polyvinylhalides, polyacrylates, polyolefins, hydrogels, and combinations thereof.

Surfaces of devices coated with the lubricious coatings of the present invention include surfaces of medical implants, indwelling medical devices, including disposable medical devices, catheters, and contact lenses, to name a few examples. This list, of course, is exemplary and not limiting.

Further objects, features and advantages of the methods, compositions and devices of the present invention, as well as a better understanding thereof, will become apparent from the following description and examples.

DETAILED DESCRIPTION

The present invention provides novel stable, multifunctional, biocompatible coating compositions which may be applied to surfaces on devices—especially medical devices—that may come into contact with a subject organism's tissues or bodily fluids. The significance of this achievement cannot be overemphasized, particularly with respect to the formation of such surfaces on synthetic materials, which are gaining ever-increasing acceptance as the materials of choice for constructing medical apparatus ranging, for example, from simple devices such as contact lenses to more complex devices including various disposable devices, catheters, guidewires, wound drainage apparatus, and longer-term indwelling implants and prosthetics.

The enhanced lubricity of the within-disclosed coatings and surfaces facilitates the insertion and removal of devices so coated (e.g. catheters), in accordance with the teachings of the present invention. The stable, biocompatible coatings applied to the surfaces of devices (e.g. medical devices) are multi-functional in that they not only impart a high degree of lubricity to the surface of the device, but also provide a crosslinked network into which other biocompatible molecules may be affixed or entrapped. These additional functionalities can be imparted to the multi-functional bioactive surfaces of the present invention through the simple additional step of linking or entrapping biocompatible agents into the crosslinked polymer network forming the surface coating. Thus, these enhanced biocompatible or bioactive properties can be achieved without sacrificing the lubricating properties of the unmodified, crosslinked surface coatings. (It should be understood that "biocompatible" agents, as that term is used herein, includes agents that may be described as "bioactive" as well.)

As noted previously, the present invention also discloses methods of making and using the within-described novel coating compositions. For example, as an added benefit, in contrast to prior art methods for coating materials with biocompatible agents, the methods of the present invention securely and stably place biocompatible agents into the physiological tissue/fluid surface layer interface where they can be active without having to be physically separated from the coating and suspended or dissolved into solution, via entrapping or "suspending" those agents within a stable, crosslinked network or lattice. This enhances the long-term activity and storage capacity of articles and devices so treated. This is a particularly advantageous aspect of the present invention for use with lubricity-enhancing agents (e.g. PVP) and with antithrombogenic agents (e.g. heparin).

Thus, in a preferred aspect, the methods of the present invention can be understood to encompass simple methods for producing stable, lubricious, biocompatible surfaces on a variety of articles or devices (e.g. medical devices). The coating compositions and articles/devices coated with same are also described in greater detail hereinbelow.

A. Coating Compositions

In particular, the invention discloses compounds comprising coupling agents having multifunctional groups which are able to react with functional (reactive) groups of other molecules (e.g. polyfunctional molecules or polymers) to form a stable, crosslinked network which can be engineered to have a variety of useful characteristics, including increased lubricity. For example, other useful molecules— such as antimicrobial agents—may be entrapped within the crosslinked network formed by the interaction between a coupling agent and a polyfunctional polymer of the present invention.

An exemplary embodiment of the present invention utilizes polyfunctional molecules, coupling agents, and biocompatible molecules (e.g. molecules that enhance lubricity) in a coating composition. Thus, in accordance with the teachings of the present invention, a coating composition can be bonded to the surface(s) of devices through the simple step of placing a solution of coating composition into contact with the surface(s) and allowing the surface(s) to incubate in the solution(s) at ambient conditions for a sufficient period of time for the composition to bond with the surface(s). Useful methods of applying compositions—e.g. "one-dip" and "two-dip" methods—are described in greater detail in Section B below and in the Examples.

Polyfunctional molecules—e.g. polymers with multifunctional groups—are preferred for use according to the present invention. Polyfunctional molecules such as polyethylenimine (PET), polyvinyl alcohol, polyacrylic acid, and polyacrylamide are particularly useful. (Polyfunctional molecules may alternatively be referred to herein as multifunctional molecules.)

The polyfunctional polymers (or molecules) may be oligomers or polymers having an average molecular weight that spans a broad range. For example, polyfunctional molecules useful as disclosed herein may have an average molecular weight in the range of about 600 to 2,000,000, preferably in the range of about 10,000 to 1,000,000 and more preferably in the range of about 20,000–30,000.

Polymers tend to be most advantageous for use herein, is the use of polymers allows the preparation of water-based formulations as the polymer either tends to be soluble in water or may be prepared as a water-based dispersion or emulsion. The use of polymers also avoids the potential toxicity caused by some monomers.

Useful molecules according to the present invention may include those having a rather broad range of equivalent weights, as well. For example, the equivalent weight of a polyfunctional polymer of the present invention is 10,000 or less, preferably 3000 or less, more preferably 2000 or less, and even more preferably 1000 or less. In various preferred embodiments of the disclosed invention, the preferred equivalent weight of a polyfunctional polymer is 200 or less, with a range of 100 or less being particularly preferred. Determination of the "equivalent weight" of a molecule, as that expression is used herein, is described hereinbelow.

As noted previously, coating compositions of the present invention also include coupling (or crosslinking) agents. Preferred coupling agents according to the present invention possess functional (reactive) groups that are capable of reacting/interacting with those of a polyfunctional molecule and a substrate molecule. Coupling agents having a functionality of two (2) or more are preferred—i.e., the molecules possess at least two functional groups. As used herein, the term "polyepoxide" means reactive polyfunctional epoxides having at least two epoxy moieties per molecule.

Useful coupling agents include epoxides—and especially polyepoxides. As used herein, the term polyepoxides includes diepoxides, triepoxides, tetraepoxides, and so forth. Examples of useful polyepoxides include, without limitation, polyglycidyl esters and/or ethers, e.g. diglycidyl butanediol ester, ethanediol diglycidyl ester, erythritol anhydride (EDE), butanediol diglycidyl ether (GAB), epichlorhydrin, and the like. Mixtures of two or more coupling agents—as well as compositions including a single species of coupling agent—are contemplated for use according to the present invention.

Among the examples of the crosslinking agents, polyepoxides are particularly preferred. Polyglycidyl ester and ether compounds are exemplary molecules useful in many of the preferred compositions of the present invention. Some examples include ethylene glycol diglycidyl ether, propylene glycol diglycidyl ether, glycerol-1,3-diglycidyl ether, glycerol triglycidyl ether, polyamine epichlorohydrin resin, polyamide polyamine epichlorohydrin resin.

Coupling agents useful according to the present invention also include glycidol derivatives, isocyanates, aldehydes and carbodiimides, to name a few examples. When the polyfunctional molecule comprises polyvinyl alcohol, polyacrylic acid and/or polyacrylamide, coupling agents such as isocyanates, aldehydes and carbodiimides are preferred. If the polyfunctional molecule comprises polyethylenimine (PEI), glycidyl derivatives are preferred coupling agents to be used therewith.

Examples of isocyanates useful according to the present invention include toluene diisocyanate, diphenylmethane diisocyanate, dicyclohexylmethane diisocyanate, and hexamethylene diiusocyanate. Examples of carbodiimides and aldlehydes useful as disclosed herein include dicyclohexylcarbodiimide, formaldehyde, and glutaraldehyde, to name but a few.

Examples of glycidol derivatives useful for practicing the present invention include compounds such as glycidyl ethers and glycidyl esters (which encompasses diglycidyl ethers and esters, as well as polyglycidyl ethers and esters). Examples of polyglycidyl ether compounds include ethylene glycol diglycidyl ether, propylene glycol diglycidyl ether, glycerol-1,3-diglycidyl ether, glycerol triglycidyl ether, polyethylene glycol diglycidyl ether and 1,6-hexanediol diglycidyl ether, to name a few.

The epoxy groups of such ethers and esters react with a wide range of chemical moieties—e.g. amino, carboxyl, and hydroxy groups—which makes them particularly useful as disclosed herein. Some other compounds and moieties with which the epoxy groups react include water, alcohol, phenol, organic acids and organic acid salts, acid anhydrides, primary amines, secondary amines, tertiary amines, acetal, acetylene, alkyl halides, 2-aminothiols, ethylene imine, ketones, phosphines, thiol, amide, acyl halide, azide, ammonia, carbon dioxide, benzene, sulfur dioxide, bismuth halide, carbon disulfide, silicon tetrahalide, and hydrogen sulfide, to name but a few.

Glycidol derivative compounds useful as disclosed herein are readily available from a variety of commercial sources. For example, a family of glycidol derivatives is available under the trade name DENACOL from Nagase Chemicals Ltd., Japan and includes mono-, di-, and tri-glycidyl ethers, glycidyl esters, and various N-glycidyl compounds (e.g. glycidyl phthalimide).

Useful coupling or crosslinking agents thus include diglycidyl, triglycidyl, and tetraglycidyl ethers and esters. Some specific examples of the foregoing include, without limitation, sorbitol polyglycidyl ether, polyglycerol polyglycidyl ether, pentaerythritol polyglycidyl ether, diglycerol polyglycidyl ether, triglycidyl tris(2-hydroxyethyl) isocyanurate, glycerol polyglycidyl ether, trimethylolpropane polyglycidyl ether, resorcinol diglycidyl ether, glycidyl ester ether of p-hydroxybenzoic acid, hydroquinone diglycidyl ether, neopentyl glycol diglycidyl ether, and 1,6-hexanediol diglycidyl ether.

Further examples include, without limitation, bisphenol A $(PO)_2$ diglycidyl ether, bisphenol S diglycidyl ether, hydrogenated bisphenol A diglycidyl ether, ethylene polyethylene glycol diglycidyl ether, propylene polypropylene glycol diglycidyl ether, polytetramethylene glycol diglycidyl ether, adipic acid diglycidyl ester, terephthalic acid diglycidyl ester, o-phthalic acid diglycidyl ester, and higher dicarboxylic acid diglycidyl ester.

The "equivalent weight" of a molecule, as that expression is used herein, may be readily determined according to methods known in the art. For example, dividing the molecular weight of a molecule by the number of functionalities (or functional groups) of that molecule provides its equivalent weight. When expressed as a formula, the equivalent weight is determined as follows:

$$\text{Equivalent weight} = \frac{\text{molecular weight}}{\text{number of functionalities}}$$

The coating compositions of the present invention interact with the surfaces of devices—e.g. medical devices—to form the underlying crosslinked base layer in accordance with the teachings of the present invention. It should be emphasized that an additional advantage of these compositions is that they are relatively non-toxic and have a high affinity toward the surfaces of the devices to be coated. These same coating materials can have additional biocompatible agents incorporated into the crosslinked network (or lattice or "web") formed via the interaction of the crosslinking agent and the polyfunctional polymer. For example, useful biocompatible agents include lubricity-enhancing agents and molecules. Antimicrobial agents, antithrombotic agents, and other biocompatible agents may also be incorporated into the coatings of the present invention.

Although solubility in water is often a preferred characteristic, it is not a required parameter of a useful polyfunctional or crosslinking molecule according to the present invention. While water-soluble molecules tend to be preferred for environmental-compatibility reasons, it is not essential that the molecules, compositions or coatings of the present invention be water-soluble.

In various applications of the within-disclosed invention, organic solvents may be preferred for use. For example, the coating of certain synthetic; surfaces with the compositions of the present invention is enhanced significantly by the use of an organic solvent to produce a more wettable—and thus more useful—coating composition.

Solvents of the present invention are preferably compatible with the device to be coated. In some applications, water is a preferred solvent. In other applications, an organic solvent is preferred. In still others, a combination of organic solvents or a combination of organic solvent and water is preferred. For example, with respect to TEFLON surfaces, a combination of water and alcohol is one preferred solvent, as alcohol confers greater "spreadability" on some surfaces, particularly those containing TEFLON.

Coating compositions of the present invention may also be described in terms of various ranges and ratios of the molecules included in those compositions,. Thus, in various preferred embodiments, molar ratios of the molecules are used; specifically, the molar ratios of the relevant functional groups are used. The calculations for the polyfunctional and coupling molecules are essentially the same, as follows:

$$\# \text{ of functional groups} = \frac{\text{Molecular weight}}{\text{Equivalent weight of molecule}}$$

Thus, depending on the polyfunctional and crosslinking (coupling) molecules used, the ratio of crosslinker:polyfunctional molecule (e.g. polyfunctional amine) ranges from 10:1 to 0.1:1. In various preferred embodiments, the ratio of crosslinking agent to polyfunctional molecule is 2:1 by weight.

The coating compositions of the present invention may further comprise a hydrophilic molecule or compound which enhances the lubricity of the coating. Suitable hydrophilic compounds include, but are not limited to, PVP and copolymers of PVP.

The coating composition may also include co-solvents or other additives to facilitate high-quality film formation. For example, such molecules include plasticizers, antifoaming agents, anticrater agents, and coalescing solvents. Other additives include, as noted previously, biocompatible agents, antimicrobial agents, antithrombotic agents,, antibiotics, and lubricity-enhancing molecules, to name a few examples. Details regarding the selection of appropriate ingredients and the amounts to use are known to those of skill in the art and will thus not be repeated herein.

B. Methods of Preparing and Applying Coating Compositions

The "basic" coating compositions of the present invention are prepared by combining a polyfunctional polymer with a crosslinking (coupling) agent, as described herein. In a preferred embodiment, a coating demonstrating superior lubricity is prepared by admixing a polyfunctional polymer, a crosslinking agent, and a biocompatible (e.g. lubricity-enhancing) agent such as PVP, wherein the latter becomes entrapped within the crosslinked network formed by the polymer and coupling agent. The coating compositions of the present invention are typically applied to a device or article using techniques known to those of skill in the art, such as spray coating, dip coating, roll coating, and the like.

For example, if a dip coating method is used, the device or article is immersed in a bath containing the coating composition and is then removed. The device may be left in the bath for a predetermined amount of time if appropriate—e.g. from about 1 second to several minutes, or even an hour or more—to obtain a coating having the desired thickness and/or other predetermined properties (e.g. lubricity).

Depending on the nature of the components of the coating composition, the article to be coated, and the application for which the coated article is to be used, a broad range of coating thicknesses may be useful. Those of skill in the art will recognize that in some applications, coatings that are an angstrom or less in thickness may be appropriate for use, whereas thicker coatings are appropriate for use in other applications.

The order in which the various components of the coating compositions of the present invention are applied may also vary, as may the number of "dips," layers, coats, etc. As illustrated in Example 1 below, "one-dip" or "two-dip" methods are commonly used to coat various articles such as medical devices. In one variation of the one-dip method, the surface of a device is dipped in a coating composition including a crosslinking agent and a polyfunctional molecule. In another variation, the composition into which the surface is dipped includes a crosslinking agent, a polyfunctional molecule, and a biocompatible agent—e.g. a lubricity-enhancing agent.

Other variations include "two-dip" methods, as noted above. In one such method, a surface is first dipped into a solution containing a crosslinking agent. Subsequently, the surface is dipped into an admixture of a polyfunctional molecule and a biocompatible agent. Alternatively, the surface may first be dipped into an admixture of a polyfunctional molecule and a biocompatible agent, followed by dipping said surface into a crosslinking agent. Other combinations and dipping orders of the three main components of the coating compositions—i.e. the crosslinking agent, the polyfunctional molecule, and the biocompatible agent—may also be used advantageously, as those of skill in the art will readily appreciate.

Additional "dipping" steps may take place in order to produce thicker coatings or to add additional biocompatible agents to the coatings previously added to the surfaces. It is generally preferable, however, to use the one-dip or two-dip methods described herein.

Wet-coated articles may be coated using any conventional method and may also be allowed to cure (or dry) for a predetermined period of time. Drying may be carried out simply by allowing the coated device or article to cure under ambient conditions. Alternatively, the process may be accelerated by the use of gentle heating, e.g., at temperatures in the range of about 27° C.–100° C. In various embodiments disclosed herein, a preferred curing temperature is in the range of about 60–70° C., with 65° C. being particularly preferred for certain applications. For some crosslinking agents, the use of higher temperatures and/or irradiation (e.g. UV irradiation) may be needed.

In various preferred embodiments, the range of temperatures that is useful in "curing" the coatings ranges from room temperature (r.t.) to about 150° C. It is preferable not to exceed 150° C. A preferred range of temperatures for curing or "setting up" the coating compositions is about 15–95° C. A more preferred range is about 20–90° C., with a range of 20–65° C. being even more preferred.

As those of skill in the art will appreciate, as the curing temperature increases, the curing time tends to decrease. Thus, compositions cured at room temperature will have a longer curing time than will compositions cured at 60° C. Those of skill in the art will also appreciate that other factors affect the time period during which coating compositions are formed and cured, such as the concentrations, molar ratios, or equivalent weights of the components of the composition (e.g. the polyfunctional polymer, coupling agent and biocompatible agent), the pH of the solution or admixture, the nature of the surface to be coated, and the like.

Other factors should be considered when preparing and using coating compositions. For example, the concentration of the polyfunctional polymer and of the crosslinking (or coupling) agent may be a relevant consideration. A currently preferred range of concentrations for polyfunctional molecules—e.g. PEI—is about 0.1–1.0% w/v. With respect to crosslinking agents—e.g. glycidyl derivatives—a preferred range is about 0.1–5% w/v.

In addition, the coatings of the invention may be prepared and applied across a broad pH range. While the coatings may be prepared and applied at any pH, a useful range is 7–12, as basic pH is often desirable. As with temperature, variations in pH may affect curing time, but such variations do not impede the coating process or the adherence of the coating composition. And as noted above, since incubation (curing) time varies depending on the temperature used, about 5–30 minutes of curing time is a useful range.

An additional benefit of the methods of the present invention is their ability to produce medical devices having stable, multi-functional biocompatible surfaces utilizing relatively benign formation chemistry and procedures which are directly applicable to a wide variety of synthetic materials. In contrast to the elevated temperatures and harsh chemical conditions commonly associated with conventional coating technology described in the art, the methods of the present invention rely upon simple cross-linking and covalent bonding with reactive groups. Accordingly, the methods of the present invention can be practiced upon relatively fragile and heat-sensitive materials.

Moreover, because of the relative simplicity of the methods of the present invention, in conjunction with the benign chemistry associated therewith, it is possible to treat medical devices in accordance with the teachings of the present invention at later stages in the manufacturing process, as well as at early stages. It is even possible to apply the unique biocompatible coatings of the present invention as a final step following the assembly of single- and multi-component medical devices.

C. Incorporating Biocompatible Molecules into Coating Compositions

In accordance with the teachings of the present invention, the lubricious properties of coatings for devices intended to come into contact with a subject's tissues or bodily fluids—e.g. the tissues/fluids of a human patient—may be significantly improved or enhanced by the addition of biocompatible molecules which further enhance the lubricious properties of the presently-disclosed coatings or which provide other useful properties. One means of preparing lubricious surfaces comprises the crosslinking of polymers in order to create an insoluble coating into (or onto) which additional lubricious compounds may be incorporated.

It is also within the scope of the present invention to entrap other (or additional) biocompatible molecules into the crosslinked network. These additional aspects of the present invention endow the multi-functional coatings with additional biocompatible properties. Because of the unique physical structure of the surface coatings of the present invention, such entrapped biocompatible molecules are presented into the circulating physiological fluids contacting the medical device at the interface of the crosslinked zone rather than on the base surfaces of the device, as often happens when using devices known in the art. This enables the biocompatible components to function without having to dissociate from a "traditional" base coating.

Moreover, because the biocompatible components are entrapped within the network, they are stable and are less likely to leach from the coating. This enhances the stability of the multi-functional surfaces and facilitates their storage and operability, as the functional aspects of the coatings (and coated surfaces) of the present invention will not degrade over time, as conventional coatings do. Thus, according to the present invention, biocompatible molecules or compositions which confer other useful properties on the coatings of the present invention—e.g. antimicrobial, antibacterial, and/or other bioactive properties—may be entrapped within the lattice structure of the within-described coating compositions. Biocompatible molecules or compositions falling into one or more categories may be entrapped or embedded within the lattice; thus, coating compositions of the present invention may be polyfunctional or multifunctional in that they are both lubricious and antitmicrobial, and so forth.

For example, an antimicrobial agent may be incorporated into the crosslinked lattice of a coating composition of the present invention. An exemplary agent—chlorhexidine—and an exemplary methodology are described in Example 11 below.

By way of providing a further example, the coatings of the present invention may also comprise biocompatible agents having antithrombotic properties. Because many of the surfaces of the components of medical devices, including implants, will directly contact the patient's tissues and bodily fluids and may have a tendency to cause blood component activation (trauma), the combined effect on a patient of exposure to a variety of surfaces may pose a complex problem and may create a substantial risk of inflammatory reaction and thrombosis in that patient.

Conventional medical practices aimed at preventing thrombosis include the direct administration of anticoagulant agents such as heparin to patients who are exposed to blood-contacting medical devices and apparatus. However, while the direct administration of heparin or other anticoagulants (e.g. hirudin or citric acid) is effective al. reducing blood coagulation, it also presents the undesirable risk of uncontrollable patient bleeding. As an alternative to the systemic administration of heparin, some have endeavored to address the problem by attaching heparin directly onto the blood-contacting surfaces of tubing, containment walls and the like via chemical or physical means, in order to prevent thrombosis while minimizing the risk of uncontrolled bleeding. However, attempts to directly bind heparin or other biologically-active molecules to synthetic materials such as plastics and metals has often proven to be unsatisfactory for a variety of reasons. Many other risks and problems may be associated with the use of various biocompatible substances as coatings, such as poor film-forming properties, leaching, degradation, to name but a few. Moreover, the strategies for binding substances such as heparin may be expensive and impractical in certain applications, particularly from a manufacturing standpoint. Thus, the discovery of coating materials that are lubricious—and which may also incorporate antimicrobial, antithrombotic and/or other bioactive molecules, and which are useful with a variety of synthetic materials—solves a number of problems and improves the post-surgical prognosis of each patient undergoing procedures that place their tissues and/or physiological fluids in contact with medical devices and apparatus. As disclosed herein, molecules or compositions falling into one or more structural or functional categories may be entrapped or embedded within the lattice. Thus, coating compositions of the present invention may be polyfunctional or multifunctional in that they are lubricious and antithrombotic, and the like.

Exemplary biocompatible agents that may be coupled to or entrapped within the biocompatible surfaces of the present invention in accordance with the teachings thereof include antibacterial (or antimicrobial) agents, antihistamines, anti-inflammatory agents, anticholinergic agents, antiparasitic agents, antiviral agents, inhibitors, diagnostic agents, ophthalmic agents, chelating agents, immunosuppressive agents, antimetabolites, anesthetics, antifungal agents, amoebicidal agents, trichomonacidal agents, analgesic agents, antiarthritic agents, antiasthmatic agents, anticoagulants, anticonvulsants, antidepressants, antidiabetic agents, antineoplastics, antipsychotic agents, antihypertensive agents, muscle relaxants, proteins, peptides, hormones and lubricating agents. As noted previously, some specific examples of biocompatible molecules that may be embedded or entrapped within the lattice include heparin, citric acid, polyvinyl pyrrolidone (PVP) and dextran sulfate, to name but a few.

It should also be noted that combinations and mixtures of these various biocompatible agents may be coupled to the biocompatible surfaces as well. The entrapment or coupling of these biocompatible agents to the multi-functional surfaces of the present invention may provide them in a more stable or less-leachable form than might otherwise be possible utilizing prior art methods in which the biocompatible agents are applied without the use of linking or entrapping means.

Prior to the advent of the present invention, it was important to consider the weight ratios of entrapped biocompatible molecules to the polyfunctional molecules of the lattice-forming coating. Such considerations are essentially irrelevant with respect to the present invention. In contrast, the size of the biocompatible molecule with respect to the tightness of the lattice network is a more relevant factor. However, since the size of the 'openings' in the network is readily adjustable to accommodate the specific biocompatible molecule (or molecules) to be embedded or entrapped within the lattice, biocompatible molecules of varying sizes may easily be included in the coatings of the present invention.

The size of the openings can readily be changed by varying the concentration of the crosslinker. For example, at a fixed polyamine concentration, reducing the concentration of crosslinker results in a loose network which can accommodate large molecules. Conversely, increasing the concentration of crosslinking agent results in a tight network structure that permits only small molecules to be entrapped or bound.

Similarly, the thickness of the coating to be applied to a particular surface or device varies, depending on the nature of the lattice and that of any biocompatible molecules entrapped within that network. It is preferred that the thickness of the coating be such that it does not negatively impact the function of the coated surface or device.

D. Coated Devices/Apparatus

While the invention is often discussed in terms of increasing the lubricity of articles, devices and apparatus formed from synthetic materials, the invention is not limited to use with synthetics. Those skilled in the art will appreciate that some medical apparatus such as artificial heart valves may include both natural and synthetic materials. The present invention is equally applicable to these compound devices. The present invention can be utilized to produce stable multi-functional biocompatible surfaces on virtually all natural and synthetic materials being used to manufacture devices, whether those devices are implants or other types of apparatus.

At present, common synthetic materials utilized in the construction of medical devices include silicones, rubbers, polyethers, polysulfones, polyamides, polyimides, polyurethanes, polycarbonates, polyesters, polyvinylbalides, polyaciylates, polyolefins, hydrogels, and derivatives, blends, copolymers and multipolymers or combinations thereof It is further contemplated as being within the scope of the present invention to treat composite surfaces, resins, metals, ceramics and carbonaceous materials, as well as a variety of other natural and/or synthetic materials.

Each of these materials has its own physical and structural properties which are suitable for various applications. For example, contact lens and ocular implants are commonly formed of polyacrylates, silicone, or hydrogels. Catheters and medical tubing are commonly formed of silicones, polyamides, polyolefins, and polyvinylchlorides (PVCs). Cardiotomy reservoirs and heaters may include silicone and elastomeric gaskets and seals in conjunction with polycarbonate and metal (e.g. various alloys, metallics and stainless steel) structural components.

Extracorporeal blood conducting circuits may include combinations of all of the foregoing materials, depending upon their complexity and the number of components involved.

In spite of this complexity, it is only the surfaces of the medical devices which are intended to contact a patient's tissues or physiological fluids that preferably are treated, although for ease of manufacturing, coating/dipping of all surfaces of the devices may readily be performed. This simplifies the application of the present invention to the manufacturing processes of such devices as the methods of the present invention can be incorporated into later stage manufacturing steps following production and assembly of the devices.

Because of the varying chemical properties of these common medical device manufacturing materials, prior art methods often required that individual components be treated separately in order to achieve an effective coating. Typically, these coatings were limited to either lubricating coatings or antithrombogenic coatings or combinations of both. Covalently bonding antithrombogenic coatings using prior art techniques often involved relatively harsh conditions and strong chemical solutions or exotic polluting solvents. The methods of the present invention overcome these problems.

Some of the many useful coatings and treatments made and used in accordance with the teachings of the present invention are further described and exemplified in the following non-limiting examples.

EXAMPLES

Example 1

PVC Substrate

This example demonstrates two different ways of preparing the lubricious coating, a one step reaction and a two step reaction. For a one-step reaction, all the ingredients are added at the same time for the coating application. For a two-step reaction, substrate is first dipped in one solution (DENACOL solution), then dipped in another solution (IIEI with various hydrophilic molecules) to complete the reaction.

TABLE 1

| One Step Solution | | Two Step Solutions | |
|---|---|---|---|
| | | Solution E | |
| DENACOL 411 | 4 g | DENACOL | 4 g |
| PEI | 2 g | GENESOLV 2004 | 400 g |
| PVPK 15 | 0.4 g | Solution F | |
| PVPK 30 | 0.4 g | PEI | 2 g |
| PVPK 90 | 0.4 g | PVPK 15 | 0.4 g |
| PVPK 120 | 0.4 g | PVPK 30 | 0.4 g |
| Stannous Octoate | 0.08 g | PVPK 90 | 0.4 g |
| GENESOLV 2004 | 400 g | PVPK 120 | 0.4 g |
| | | Stannous Octoate | 0.08 g |
| | | GENESOLV 2004 | 400 g |

A. Preparation of One-step Treated PVC Tubing

Ten French PVC tubes are soaked in the one step solution for one minute, then dried in a 65° C. oven for two hours. Repeat the above process one more time before testing.

B. Preparation of Two-step Treated PVC Tubing

Ten French PVC tubes are first soaked in the solution E for one minute and are dried in a 65° C. oven for ten minutes. These tubes are then soaked in solution F for one minute and are dried for two hours in a 65° C. oven. Repeat the whole process once before testing.

C. Evaluation

The lubricity of each sample is determined by the pull force, using, for instance, a tensile strength testing instrument—e.g. an Instron instrument (Instron. Canton, Mass.)—for the measurement. Briefly, a tensile strength testing instrument of the sort used herein includes a plate (e.g. a metal or plastic plate) with a groove cut into it; the groove can be any configuration (e.g. the configuration shown in FIG. 1). The groove is preferably lined with tubing, and the sample of tubing to be tested is inserted into the lumen of the tubing-lined groove. In essence, the testing system used as described herein is designed to emulate the vascular system; the tube-lined groove simulates a blood vessel, for example.

Figure 1:
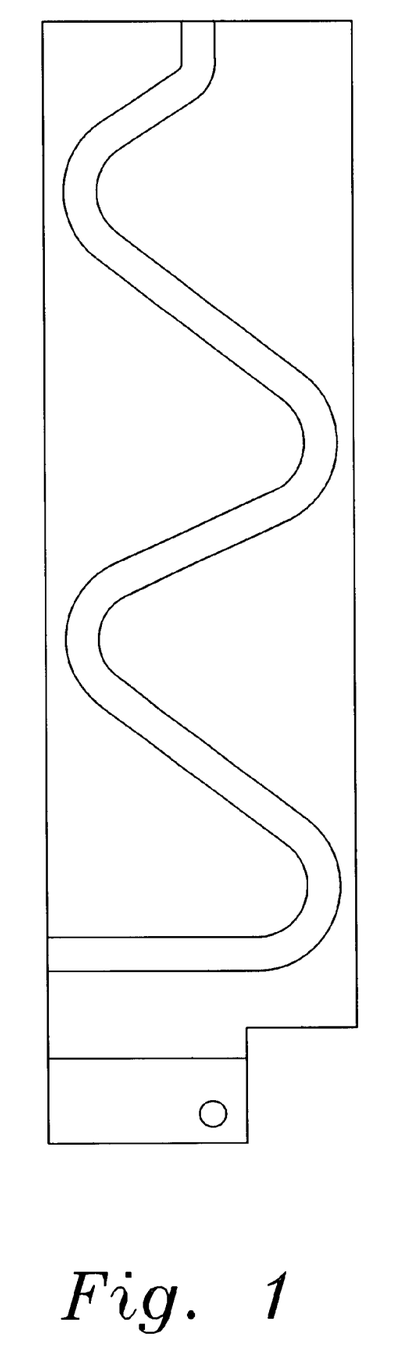
FIG. 1 illustrates a testing device with multiple curves which is utilized to determine the pull force of samples (e.g. tubing samples). Further details are provided in the Examples below.

Looking at FIG. 1, for example, a tubing-lined plate having multiple curves cut into it is shown in the configuration in which it would be suspended in the testing instrument. One portion of a motorized "jaw" attaches to the plate at the bottom, which has a hole cut into it for that purpose; the bottom portion of the "jaw" is maintained in a stable configuration and does not move. At the upper end of the plate, another portion of the "jaw" attaches to the end of the sample (test) tubing that extends from the grooved plate. As the upper portion of the "jaw" moves incrementally away from the lower portion, the tension on the sample (test) tubing increases and measurements are made during the test procedure which enable one to determine the tensile strength of the tubing so tested. Again, this is but one method of determining the tensile strength of the coatings and coated devices of the present invention; thus it should be understood that this testing method does not limit the scope of the invention in any fashion.

In a typical testing procedure, each sample is first placed inside a large tubing filled with normal saline. Then the tubing set is mounted on a testing device with multiple curves (see FIG. 1). At the cross-head speed of 5 in/min, the pull force is recorded for each sample for future comparison. For long-term coating stability evaluation, the same tube is subjected to the pull force measurement at different soaking time periods. In general, the saline is changed each time after measurement; alternatively, the saline may be changed twice during the first 30-minute soaking.

The pull forces of treated samples are measured and results are summarized as follows.

TABLE 2

| | Pull Force (lb.) | | | | | |
|---|---|---|---|---|---|---|
| | Initial | 30 Min. | 7 Days | 14 Days | 21 Days | 28 Days |
| Control (Uncoated) | >20 | >20 | | | | |
| One Step | 0.98 ± 0.24 | 1.38 ± 0.48 | 1.83 ± 0.48 | 1.65 ± 0.42 | 1.77 ± 0.46 | 2.26 ± 0.68 |
| Two Step | 0.54 ± 0.06 | 0.50 ± 0.04 | 0.48 ± 0.05 | 0.38 ± 0.03 | 0.32 ± 0.02 | 0.39 ± 0.04 |
| | 35 Days | 42 Days | 49 Days | 56 Days | 63 Days | |
| Control (Uncoated) | | | | | | |
| One Step | 2.16 ± 0.82 | 3.00 ± 0.92 | 2.59 ± 0.75 | 2.78 ± 0.95 | 3.03 ± 1.03 | |
| Two Step | 0.31 ± 0.06 | 0.44 ± 0.05 | 0.41 ± 0.04 | 0.39 ± 0.06 | 0.53 ± 0.09 | |

Example 2

Polypropylene Substrate

Polypropylene (PP) slabs are divided into two groups. One group is first coated with 1% pentacrythritol polyglycidyl ether (DENACOL 411) solution. After drying, the slab is soaked in the mixture of 0.5% (w/w) PEI, 0.5% (w/w) PVP, and 0.02% (w/w) stannous octoate solution. The other group is first soaked in a dichromate sulfuric acid solution (sodium dichromate 0.86% (w/v) for three hours.

After extensive rinsing with de-ionized water, these samples follow the same procedures of the first group. Samples from the above two groups are subject to a finger rubbing evaluation under running tap water. Samples without acid pretreatment tend to lose their lubricity within a minute. Samples with acid pretreatment maintain their lubricity even after ten minutes of rubbing.

Example 3

Polyester Substrate

1% pentaerythritol polyglycidyl ether (DENACOL 411) (w/w) solution is prepared by dissolving 4.20 g DENACOL 411 in 420 g GENESOLV 2004. Two polyethyleneimine solutions are prepared as follows:

| | Solution A | Solution B |
|---|---|---|
| PEI | 0.5 g | 1.5 g |
| PVPK 120 | 0.5 g | 1.5 g |
| Stannous Octoate | 0.05 g | 0.06 g |
| Acetic Acid | 20 g | — |
| N-Propanol | 80 g | 300 g |

Polyester films are soaked in the 1% DENACOL solution for 30 seconds and dried in a 65° C. oven for ten minutes. The films are divided into two groups, each group soaked in either solution A or B separately for an additional 30 seconds. Finally these films are dried in a 65° C. oven for at least two hours. Polyester film from each treated group is further sealed in the pouch for ETO sterilization (SPS 480 sterilization cycle). Both sterilized and non-sterilized samples from each group are rubbed under tap water for five minutes and are still very slippery.

Example 4

Silicone Substrate

Two PEI solutions are prepared as follows:

|  | Solution C | Solution D |
|---|---|---|
| PEI | 1.5 g | 1.5 g |
| PVPK 120 | 4.5 g | 4.5 g |
| Heparin complex | — | 1.5 g |
| Stannous Octoate | 0.06 g | 0.06 g |
| N-Propanol | 300 g | 300 g |

15 French silicone tubes are first immersed in a 1% DENACOL 411 solution for 30 seconds and dried in a 65° C. oven for ten minutes. Then a subgroup of these silicone tubes is soaked in solution C and the other subgroup is soaked in solution D for 30 seconds each. Both groups are dried in a 65° C. oven for two hours prior to a lubricity evaluation. Some of the tubes from each group are also sent for ETO sterilization (SPS 480 cycle).

The lubricity evaluation method is carried out as described in Example 1. Results are summarized as follows.

Example 5

Plasma Treatment

Polyethylene (PE) tubes are divided into three groups. Each group is treated with argon, nitrogen or oxygen plasma separately, using a Model MKII-1 plasma unit. The gas flow rate is 1500 cc/min for argon and nitrogen, and 1000 cc/min for oxygen. Other treatment conditions remain the same, i.e., 1000 watts for eight minutes at 100° F.

The treated PE tubes are first soaked in a 1% (w/w) pentaerythritol polyglycidyl ether (DENACOL 411/GENESOLV solution for one minute, then dried in a 65° C. oven for ten minutes. (DENACOL is a trademark of Nagase Chemicals Ltd., Japan; GENESOLV is a registered trademark of Allied Signal, Morristown, N.J.) The tubes are then soaked in a mixture of 0.5% (w/w) polyethyleneimine (PEI), 1.5% (w/w) polyvinylpyrrolidone (PJP), 0.5% (w/w) heparin complex (a variety of heparin complexes are commercially available), and 0.02% (w/w) stannous octoate n-propanol solution for one minute and dried in a 65° C. oven for at least two hours.

A set of PE tubes without plasma pretreatment is also coated in the same way for comparison. The lubricity and tensile strength of each sample is determined as described in Example 1.

For the long-term coating stability evaluation, the same tube is subjected to the pull force measurement at different soaking time periods. The saline is changed each time after measurement except the saline is changed twice during the first 30-minute soaking. The pull force of each sample is summarized in the following table.

TABLE 3

Pull Force of Lubricious-Coated Silicone Tubing With and Without Heparin Complex Before and After ETO Sterilization
Pull Force (lb)

|  | N | Initial | 30 Min. | 3 Days | 7 Days | 14 Days | 21 Days |
|---|---|---|---|---|---|---|---|
| Control (No Coating) | 3 | >20 | >20 |  |  |  |  |
| No heparin complex No ETO steri. | 3 | 1.16 ± 0.57 | 0.87 ± 0.43 | 0.90 ± 0.30 | 0.81 ± 0.41 | 0.70 ± 0.19 | 0.52 ± 0.25 |
| No heparin complex ETO steri. (SPS 480) | 3 | 1.21 ± 0.23 | 1.47 ± 0.28 | 1.23 ± 0.10 | 0.94 ± 0.16 | 0.90 ± 0.18 | 0.75 ± 0.15 |
| Heparin complex No ETO steri. | 3 | 1.94 ± 1.34 | 1.09 ± 0.43 | 1.66 ± 0.86 | 1.69 ± 0.71 | 1.90 ± 0.58 | 1.70 ± 0.59 |
| Heparin complex ETO steri. (SPS 480) | 3 | 1.05 ± 0.14 | 0.95 ± 0.15 | 1.11 ± 0.07 | 1.22 ± 0.24 | 1.31 ± 0.20 | 1.34 ± 0.13 |

|  | N | 28 Days | 35 Days | 45 Days | 48 Days | 63 Days |
|---|---|---|---|---|---|---|
| Control (No Coating) | 3 |  |  |  |  |  |
| No heparin complex No ETO steri. | 3 | 0.49 ± 0.13 | 0.79 ± 0.39 | 0.62 ± 0.06 | 0.32 ± 0.07 | 0.80 ± 0.25 |
| No heparin complex ETO steri. (SPS 480) | 3 | 0.79 ± 0.20 | 0.91 ± 0.17 | 0.86 ± 0.39 | 0.68 ± 0.21 | 0.86 ± 0.15 |
| Heparin complex No ETO steri. | 3 | 1.99 ± 1.38 | 2.12 ± 1.11 | 2.19 ± 1.42 | 2.74 ± 1.69 | 2.62 ± 1.75 |
| Heparin complex ETO steri. (SPS 480) | 3 | 1.26 ± 0.20 | 1.39 ± 0.20 | 1.27 ± 0.42 | 1.42 ± 0.38 | 1.57 ± 0.32 |

TABLE 4

| | | Pull Force (lb.) | | | | | |
|---|---|---|---|---|---|---|---|
| | N | Initial | 30 Min. | 4 Days | 7 Days | 14 Days | 21 Days |
| Control (No Coating) | 3 | >15[1]) | NA | | | | |
| PE/Lub | 3 | 6.93 ± 4.10 | 12.85 ± 1.67[2] | | | | |
| Argon plasma/Lub | 3 | 0.84 ± 0.05 | 0.73 ± 0.09 | 0.81 ± 0.08 | 0.85 ± 0.12 | 0.88 ± 0.10 | 0.86 ± 0.10 |
| Nitrogen Plasma/Lub | 3 | 0.80 ± 0.04 | 0.76 ± 0.06 | 0.78 ± 0.01 | 0.95 ± 0.11 | 0.94 ± 0.05 | 1.04 ± 0.04 |
| Oxygen Plasma/Lub | 3 | 0.83 ± 0.04 | 0.78 ± 0.03 | 0.71 ± 0.05 | 0.96 ± 0.17 | 0.88 ± 0.05 | 0.90 ± 0.06 |
| | N | 28 Days | 42 Days | 49 Days | 56 Days | 70 Days | |
| Control (No Coating) | 3 | | | | | | |
| PE/Lub | 3 | | | | | | |
| Argon plasma/Lub | 3 | 0.89 ± 0.14 | 0.88 ± 0.08 | 1.10 ± 0.35 | 1.02 ± 0.12 | 1.03 ± 0.38 | |
| Nitrogen Plasma/Lub | 3 | 1.10 ± 0.25 | 0.84 ± 0.06 | 0.87 ± 0.03 | 0.95 ± 0.14 | 0.99 ± 0.21 | |
| Oxygen Plasma/Lub | 3 | 1.00 ± 0.19 | 0.82 ± 0.04 | 0.80 ± 0.02 | 0.89 ± 0.07 | 0.84 ± 0.10 | |

[1]Tubes deformed
[2]Two tubes deformed

The stability of the lubricious coating for plasma pretreated samples is clearly demonstrated by the low pull force as compared to those of control and non-plasma pretreated samples.

Example 6

Polyurethane Substrate

Solution G is prepared essentially as follows:

| Solution G | |
|---|---|
| PEI | 1.5 g |
| PVPK 120 | 1.5 g |
| Heparin Complex | 1.5 g |
| Stannous Octoate | 0.06 g |
| N-Propanol | 300 g |

Polyurethane (PU) bitumen tubes are first soaked in 1% DENACOL 411 solution for 30 seconds. After drying the tubes in a 65° C. oven for ten minutes, the PU tubes are soaked in Solution G for 30 seconds and dried in a 65° C. oven for two hours. A portion of these tubes is also sent out for ETO sterilization (SPS 120 cycle).

The same pull test recited for Example 1 is used to evaluate the lubricity. Results are summarized as follows.

TABLE 5

| | Pull Force (lb.) | | | | | |
|---|---|---|---|---|---|---|
| | Initial | 30 Min. | 4 Days | 7 Days | 14 Days | 21 Days |
| Control (Uncoated) | >20 | >20 | | | | |
| PU (No Sterilization) | 0.47 ± 0.04 | 0.21 ± 0.03 | 0.27 ± 0.04 | 0.45 ± 0.06 | 0.64 ± 0.03 | 1.06 ± 0.26 |
| PU (ETO (SPS120)) | 0.51 ± 0.14 | 0.42 ± 0.10 | 0.48 ± 0.06 | 0.68 ± 0.21 | 1.10 ± 0.27 | 1.21 ± 0.41 |
| | 28 Days | 35 Days | 49 Days | 56 Days | 63 Days | |
| Control (Uncoated) | | | | | | |
| PU (No Sterilization) | 1.38 ± 0.53 | 1.94 ± 0.58 | 2.63 ± 1.00 | 3.32 ± 1.56 | 4.98 ± 2.65 | |
| PU (ETO (SPS120)) | 1.47 ± 0.12 | 1.93 ± 0.27 | 2.69 ± 0.26 | 3.49 ± 0.74 | 5.00 ± 1.22 | |

Example 7

Polyurethane Substrate

Solution H is prepared essentially as follows:

| Solution H | |
|---|---|
| PEI | 0.3 g |
| PVPK 120 | 0.3 g |
| Heparin Complex | 0.3 g |
| Stannous Octoate | 0.03 g |
| N-Propanol | 300 g |

Polyurethane (PU) bitumen tubes are first soaked in a 0.2% (w/w) DENACOL 411 /GENESOLV solution for 30 seconds. After drying, the PU tubes are soaked in Solution H for 30 seconds and then dried in a 65° C. oven for two hours. Then the tubes are sterilized in ETO (SPS 480 cycle).

The pull test used in Example 1 is performed. Results are summarized as follows.

TABLE 6

| | Pull force (lb.) | | | | | | |
|---|---|---|---|---|---|---|---|
| | Initial | 30 Min. | 4 Days | 7 Days | 14 Days | 28 Days | 35 Days |
| Control (Uncoated) | >20 | >20 | | | | | |
| Treated PU (ETO (SPS 480)) | 2.67 ± 2.19 | 0.75 ± 0.29 | 0.78 ± 0.37 | 0.51 ± 0.20 | 0.78 ± 0.57 | 0.67 ± 0.34 | 0.79 ± 0.30 |

Example 8

15 French Polyvinyl Chloride Substrate

| Solution I | |
|---|---|
| PEI | 0.3 g |
| PVPK 120 | 0.9 g |
| Heparin Complex | 0.3 g |
| Stannous Octoate | 0.03 g |
| N-Propanol | 300 g |

15 French polyvinyl chloride (PVC) tubes are first soaked in a 0.2% (w/w) DENACOL 411/GENESOLV solution for 30 seconds. After drying, these PU tubes are soaked in Solution I for 30 seconds and dried in a 65° C. oven for two hours. A portion of these tubes is sterilized in ETO (SPS 480 cycle).

The pull test used in Example 1 is performed. Results are summarized as follows.

coated slabs are placed under the flowing tap water with extensive finger rubbing for ten minutes. The stability of the lubricious coating is demonstrated by a continued slipperiness as compared to the uncoated slabs.

Example 10

Demonstration of Entrapment of Biomolecules in Lattice

The effectiveness of the current lubricious interpenetration network to retain biocompatible molecules such as heparin complex after leaching with albumin solution can be demonstrated in the following examples. Ten French PVC and 15 French silicone tubes are soaked in 1% DENACOL solution for 30 seconds and dried in a 65° C. oven for ten minutes. These tubes are then soaked in Solution G for 30 seconds and dried in a 65° C. oven. The whole process is repeated one more time before testing. For comparison, a

TABLE 7

| | Pull force (lb.) | | | | | | |
|---|---|---|---|---|---|---|---|
| | Initial | 30 Min. | 4 Days | 7 Days | 14 Days | 28 Days | 35 Days |
| Control | >20 | >20 | | | | | |
| 15 Fr. PVC (No ETO) | 1.67 ± 0.85 | 2.02 ± 1.59 | 2.45 ± 2.11 | 2.71 ± 1.98 | 2.62 ± 1.48 | 3.00 ± 1.67 | 3.80 ± 2.0 |
| 15 Fr. PVC (with ETO (SPS480)) | 1.83 ± 0.11 | 1.88 ± 0.18 | 1.90 ± 0.07 | 1.96 ± 0.50 | 2.06 ± 0.38 | 2.27 ± 0.37 | 2.24 ± 0.51 |

Example 9

PEBAX Substrate

Two different kinds of PEBAX slabs, 4033SA01 (hardness 40D) and 2533SA01 (hardness 25D) were received from Elf Atochem. The PEBAX slabs are first immersed in 1% DENACOL 411 solution for 30 seconds and dried in a 65° C. oven for ten minutes. Then these PEBAX slabs are soaked in Solution B as described in Example 3 for 30 seconds and dried in a 65° C. oven for two hours. These 0.5% (w/w) heparin complex only solution is also used to coat ten French PVC and 15 French silicone and dried in a 65° C. oven for two hours before testing.

Samples from each group (lubricious coating and heparin complex, and heparin complex only) are placed in the 5% human albumin tris/saline buffer for the leaching study. After dynamic shaking at 37° C. for different periods of time, samples of the solution are taken to detect the amount of leached heparin in the solution. Results of detected heparin at different time periods for each material are summarized as follows.

TABLE 8

| | | Heparin Activity (Unit/ml) Leaching Time (hr.) | | | | | | |
|---|---|---|---|---|---|---|---|---|
| | N | 0.5 | 1 | 2 | 4 | 24 | 48 | 96 |
| PVC (Lubricious + heparin complex) | 2 | 0 | 0.21 ± 0.30 | 0.55 ± 0.16 | 0.36 ± 0.17 | 0 ± 0 | 0.39 ± 0.06 | 0.52 ± 0.08 |
| PVC (heparin complex) | 3 | 16.93 ± 8.13 | 18.07 ± 9.08 | 19.80 ± 10.17 | 18.07 ± 9.00 | 16.63 ± 9.45 | 15.61 ± 8.88 | 13.87 ± 7.49 |

TABLE 8-continued

| | | Heparin Activity (Unit/ml) Leaching Time (hr.) | | | | | | |
|---|---|---|---|---|---|---|---|---|
| | N | 0.5 | 1 | 2 | 4 | 24 | 48 | 96 |
| Silicone (Lubricious + heparin complex) | 2 | 0.96 ± 0.08 | 0.90 ± 0.39 | 1.24 ± 0.11 | 1.43 | 0.86 ± 0.22 | 0.90 ± 0.09 | 1.04 ± 0.05 |
| Silicone (heparin complex) | 3 | 27.93 ± 5.66 | 27.17 ± 4.11 | 27.49 ± 5.22 | 24.36 ± 5.60 | 22.85 ± 6.85 | 20.35 ± 7.01 | 17.45 ± 6.93 |

As shown in the above table, for the non-coated samples the heparin is almost completely leached out during the first half hour in contact with the 5% human albumin tris/saline buffer. In contrast, samples first coated with the lubricious coating and heparin showed a significant less amount of leaching for each time period tested all the way to 96 hours of shaking with the same solution. This observation is found true for both PVC and silicone substrates.

As the foregoing examples illustrate, the present invention is broadly applicable to a wide variety of articles and devices for medical and non-medical uses, including multicomponent extracorporeal blood conducting circuits. In contrast to prior art techniques, the present invention is able to completely treat the interior surfaces of such devices and blood conducting circuits following manufacture and assembly so that only the surfaces intended to contact a patient's physiological fluids are treated. Moreover, the treating conditions are benign relative to prior art treatments such that the manufacturer need not worry about damaging susceptible components of the assembled devices. Nonetheless, it should be emphasized that the surfaces of medical implants and indwelling medical apparatus may also be treated in accordance with the teachings of the present invention through simple immersion in a treating solution for the appropriate incubation period.

The foregoing demonstrates that the methods of the present invention produce unique medical devices having previously unobtainable stable, multi-functional biocompatible surfaces. These methods are particularly applicable to the reduction of antithrombogenic surfaces on medical devices for use in contact with a patient's blood.

Example 11

Inclusion of Antimicrobial Agent in Lattice

As disclosed herein, a variety of biocompatible agents may readily be incorporated into the crosslinked lattices of the coating compositions of the present invention. The following is an example of the use of an antimicrobial agent in such an application.

Polyurethane tubes are soaked in 1% Denacol solution for 30 seconds and subsequently dried in an oven at 65° C. for 10 minutes. The tubes are then exposed to a solution consisting of 1.5 g PEI (Lupasol), 1.5 g PVP, 3.0 g Chlorhexidine acetate, 0.06 g stannous octoate, and 300 g n-propanol for 30 seconds and then cured in an oven at 65° C. for 2 hours.

To evaluate the stability and effectiveness of the coating, the coated tubes are first exposed to 2% FBS for 5 days to remove unbonded and loosely-bonded chlorhexidine. After exposure to FBS, the tubes are then exposed to bacterial solutions (0.1 ml of 104/ml) in the presence of FBS in MEM. A reduction of 99.992% for *Staphylococcus aureus* and a reduction of 98.4% of *Pseudomnonas aeruginosa* was noted after 24 hours of exposure in exemplary trials of this procedure.

Thus, it should be understood that the embodiments of the present invention disclosed herein are not limiting but rather illustrative of the principles of the present invention and that other modifications may be employed which are within the scope thereof. Accordingly, the present invention is limited only by the appended claims.

We claim:

1. A stable, lubricious, biocompatible coating composition comprising a coupling agent, a polyfunctional polymer and at least one biocompatible agent, wherein said coupling and said polyfunctional polymer are in a ratio ranging from 10:1 to 0.1:1, and wherein said coupling agent and said polymer chemically interact to form a three-dimensional crosslinking network which is capable of physically entrapping said biocompatible agent.

2. The composition of claim 1, wherein said coupling agent is capable of chemically linking said polyfunctional polymer to the surface of a medical device.

3. The composition of claim 1, wherein said polyfunctional polymer has two or more functionalities.

4. The composition of claim 1, wherein said polyfunctional polymer has an equivalent weight of 100 or less.

5. The composition of claim 1, wherein said coupling agent has an epoxy functionality of two (2) or greater.

6. The composition of claim 1, wherein said polyfunctional polymer is selected from the group consisting of polyethylenimine, polyvinyl alcohol, polyacrylic acid, and polyacrylamide.

7. The composition of claim 1, wherein said coupling agent comprises one or more epoxides.

8. The composition of claim 7, wherein said one or more epoxides are polyepoxides.

9. The composition of claim 7, wherein said one or more epoxides are polyglycidyl ether compounds.

10. The composition of claim 9, wherein said polyglycidyl ether compounds are selected from the group consisting of diglycidyl ethers, triglycidyl ethers, and tetraglycidyl ethers.

11. The composition of claim 7, wherein said one or more epoxides are selected from the group consisting of sorbitol polyglycidyl ether, polyglycerol polyglycidyl ether, pentaerythritol polyglycidyl ether, diglycerol polyglycidyl ether, triglycidyl tris(2-hydroxyethyl)isocyanurate, glycerol polyglycidyl ether, trimethylolpropane polyglycidyl ether, resorcinol diglycidyl ether, glycidyl ester ether of p-hydroxybenzoic acid, hydroquinone diglycidyl ether, neopentyl glycol diglycidyl ether, 1,6-hexanediol diglycidyl ether, bisphenol A (PO)$_2$ diglycidyl ether, bisphenol S diglycidyl ether, hydrogenated bisphenol A diglycidyl ether, ethylene polyethylene glycol diglycidyl ether, propylene polypropylene glycol diglycidyl ether, polytetramethylene glycol diglycidyl ether, adipic acid diglycidyl ester, terephthalic acid diglycidyl ester, o-phthalic acid diglycidyl ester, and higher dicarboxylic acid diglycidyl ester.

12. The composition of claim 1, wherein said coupling agent is selected from the group consisting of isocyanates, aldehydes and carbodiimides.

13. The composition of claim 12, wherein said isocyanates are selected from the group consisting of toluene diisocyanate, diphenylmethane diisocyanate, dicyclohexylmethane diisocyanate, and hexamethylene diisocyanate.

14. The composition of claim 1, wherein said biocompatible agent is a hydrophilic polymer.

15. The composition of claim 14, wherein said hydrophilic polymer is selected from the group consisting of polyvinylpyrrolidone (PVP), PVP/vinyl acetate copolymer, and polyethylene oxide.

16. The composition of claim 1, wherein said biocompatible agent is selected from the group consisting of antibacterial agents, antimicrobial agents, antihistamines, antiinflammatory agents, anticholinergic agents, antiparasitic agents, antiviral agents, inhibitors, diagnostic agents, ophthalmic agents, chelating agents, immunosuppressive agents, antimetabolites, anesthetics, antifungal agents, amoebicidal agents, trichomonacidal agents, analgesic agents, antiarthritic agents, antiasthmatic agents, anticonvulsants, antidepressants, antidiabetic agents, antineoplastics, antipsychotic agents, antihypertensive agents, muscle relaxants, proteins, peptides, hormones and lubricating agents.

* * * * *